United States Patent [19]
Rudy

[11] Patent Number: 5,435,323
[45] Date of Patent: Jul. 25, 1995

[54] DEVICE AND METHOD FOR SECURING PATIENT TO TRAUMA BOARD

[76] Inventor: Walter R. Rudy, 903 N. Elder St., Bloomington, Ill. 61701

[21] Appl. No.: 208,975

[22] Filed: Mar. 10, 1994

[51] Int. Cl.⁶ .............................................. A61F 5/37
[52] U.S. Cl. .................................... 128/870; 5/628
[58] Field of Search ............... 128/869, 870, 871, 845; 5/82 R; 602/4, 5, 32, 35, 36

[56] References Cited

U.S. PATENT DOCUMENTS

| | | | |
|---|---|---|---|
| 2,215,454 | 9/1940 | Condit | 128/870 |
| 3,046,982 | 7/1962 | Davis | 128/134 |
| 3,258,788 | 7/1966 | Anciaux | 5/82 |
| 3,707,734 | 1/1973 | Matthews | 5/82 |
| 3,737,923 | 6/1973 | Prolo | 5/82 |
| 3,889,668 | 6/1975 | Ochs | 128/870 |
| 4,369,982 | 1/1983 | Hein et al. | 280/47.13 R |
| 4,400,820 | 8/1983 | O'Dell et al. | 378/209 |
| 4,473,912 | 10/1984 | Scheidel et al. | 5/82 |
| 4,601,075 | 7/1986 | Smith | 128/870 |
| 4,612,678 | 9/1986 | Fitsch | 5/82 |
| 4,779,858 | 10/1988 | Saussereau | 269/328 |
| 5,027,833 | 7/1991 | Calkins | 128/870 |
| 5,048,134 | 9/1991 | Dennill | 128/870 |
| 5,058,575 | 10/1991 | Anderson | 128/87 R |
| 5,083,574 | 1/1992 | Schlutow | 128/870 |
| 5,121,514 | 6/1992 | Rosane | 5/628 |
| 5,146,641 | 9/1992 | Zwickey | 5/628 |
| 5,148,815 | 9/1992 | Britton | 128/870 |
| 5,179,746 | 1/1993 | Rogers | 5/625 |
| 5,190,055 | 3/1993 | O'Connor | 128/869 |
| 5,201,089 | 4/1993 | Ferreira | 5/627 |
| 5,211,185 | 5/1993 | Garth et al. | 128/870 |
| 5,211,186 | 5/1993 | Shoemaker | 128/870 |

*Primary Examiner*—Michael A. Brown
*Attorney, Agent, or Firm*—Marshall, O'Toole, Gerstein, Murray & Borun

[57] ABSTRACT

A patient transport body and head restraint device and method for securing a patient to a trauma board. The body restraint device includes an assembly comprising two primary straps and a secondary strap where each primary strap is positioned along a side of the trauma board. The primary straps are drawn together by the secondary strap. The patient's head is restrained by a headrest and hold-down member which restrains the head while allowing access to a patient's head, eye and nose areas.

16 Claims, 4 Drawing Sheets

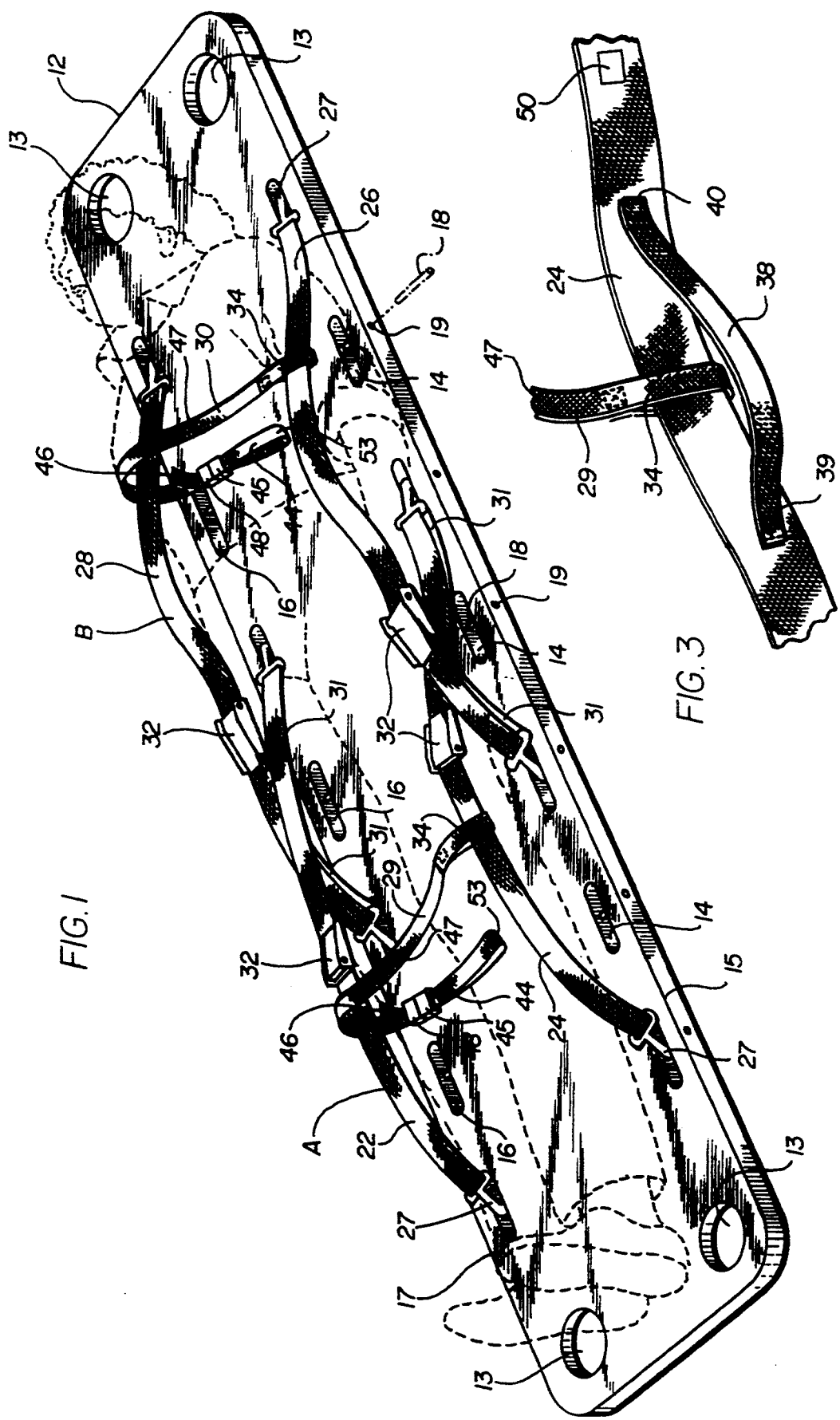

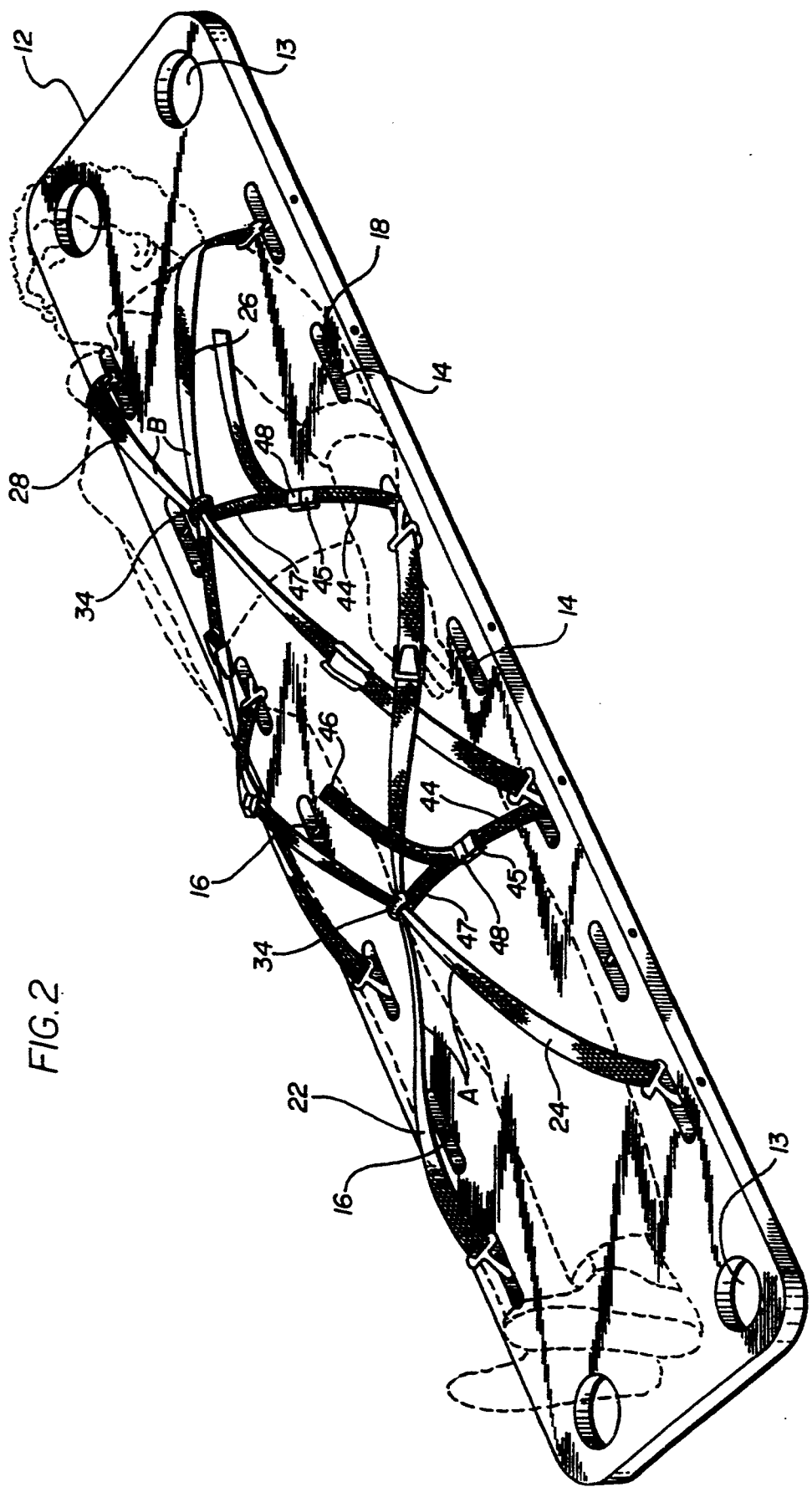

DEVICE AND METHOD FOR SECURING PATIENT TO TRAUMA BOARD

FIELD OF INVENTION

The present invention relates to a patient transport body and head hold-down system and more particularly to a device and method for securing and restraining a patient, such as an accident victim, on a patient body board while transporting the patient from a first, accident or other site to a treatment center.

BACKGROUND OF THE INVENTION

Various devices heretofore have been employed to immobilize a patient's body and head while transporting the patient from an accident or other site to a second treatment site such as a hospital emergency room. Often, in the case of an automobile accident or industrial injury, the patient must be transported from the injury scene to a medical facility under adverse conditions involving time, stress, weather, and/or darkness. In transporting a patient, paramedics or other medical personnel necessarily seek to minimize aggravation of injuries to a patient's cervical spine, head and neck. To accomplish this end, a patient must be secured relatively readily and efficiently on a patient body and head hold-down board, often referred to as a back or trauma board.

While various systems are available for maintaining and restraining a patient's body and head from movement during patient transport, problems prevail. It has been found with some conventional patient restraint systems, that the flexible webbed straps utilized to immobilize a patient on a trauma board extend transversely across the board. Prior to placing a patient on the board, various straps have to be moved away from the board so that the patient can be placed on the board without any hold-down straps resting under the patient. It can be appreciated that if a strap is inadvertently located on a board beneath the patient, the patient has to be moved to recover the webbed strap. This problem of strap misplacement is particularly prevalent at night at an accident scene, where proper lighting to check strap location sometimes is not available.

Additionally, it has been found that with some patient hold-down systems presently available, there are an excessive number of strap tails or buckles with which a paramedic or other medical person must contend to properly secure a patient to a trauma board. This problem often manifests itself at the location of a drowning site or other location involving water or snow where the strap tails get wet or covered with ice. Other hold-down systems utilize velcro connectors which are not always satisfactory particularly if the connectors come in contact with body fluids such as blood. It is difficult to decontaminate the velcro fasteners of such bodily fluids.

Further, various restraint systems available today utilize metal buckles or other fastening means which interfere with various radiological procedures such as an x-ray. On occasion, a patient will be brought to a medical treatment center where, prior to removing the patient from the trauma board, medical personnel choose to x-ray the patient to ascertain the nature and extent of a patient's injuries. Unfortunately, the metal components of the hold-down devices interfere with the x-ray, CAT scans or other medical procedures in that the metal components of the hold-down system tend to scatter the x-ray beam thereby providing an erroneous x-ray reading.

Similarly, various patient head and neck restraining devices are unsatisfactory because they limit access to the patient's head, eyes, ears, mouth or neck during examination and/or treatment. With other systems presently available, the patient restraints are not satisfactory because they must be either loosened excessively or completely removed to allow for an appropriate medical examination.

What is desired is to alleviate the disadvantages attendant with various prior art patient hold-down and immobilization devices. It is particularly desired to have a patient restraining device and system for relatively readily securing and restraining a patient to a trauma board utilizing flexible, webbed or other non-porous straps which do not suffer the disadvantages of being lodged under a patient or trailing from the trauma board. It also is desired to have a system whereby a patient can be strapped to a trauma board relatively easily but, yet, very effectively whereby the patient is properly immobilized. Moreover, it is desired that a patient's head be relatively readily accessible to medical personnel while the patient's head is restrained on the trauma board.

Finally, it also is desired that the components of the patient trauma board retention device be made of materials which do not interfere with the x-ray or other radiological procedures carried out on a patient while the patient is restrained to a trauma board.

SUMMARY OF THE INVENTION

The invention disclosed and claimed herein serves to obviate various disadvantages associated with conventional devices for restraining and immobilizing a patient on a trauma board and to achieve the desires previously expressed for a patient hold-down device and system.

Briefly, the present invention generally comprises the use of two strap assemblies, each assembly comprising a pair of primary tension straps and a secondary tension strap attached to one of the primary straps. The trauma board upon which a patient is secured generally is a conventional, substantially flat board having a series of openings located on the periphery of the board. Preferably, conventional speed clip pins are predominantly located in the various openings. A speed clip pin is a metal pin that is fixed in a plastic rod-like member which is removably positioned in a board opening and serves as a board mounting means for a strap.

Each primary strap is a flexible, webbed member approximately two inches in width. Fully extended, the strap is approximately four feet long; however, upon actuation of a conventional sliding lever buckle, the effective strap length can be selectively reduced to approximately eighteen inches. The primary strap is adjusted by sliding a conventional lever buckle along the length of the strap webbing. The primary strap has a conventional fixed clip at each of its two ends, each clip being adapted to snap onto a board speed pin.

A first primary strap is aligned longitudinally along one side of the trauma board and the respective ends of the primary strap are clipped or snapped into spaced board speed pins on one side of the board. The primary strap lever buckle is adapted to slide along the length of the web of the primary strap to tension or otherwise cinch the primary strap to the board by varying the length of the strap to what is referred to herein as the effective strap length.

The remaining primary strap, forming the first pair of primary straps, is placed on the opposite side of the board across from the first primary strap and extends longitudinally along the opposite side of the board. The remaining primary strap ends are fastened to spaced speed pins on the opposite side of the board and the strap buckle lever serves to cinch or tension the strap whereby the primary strap is positioned substantially parallel and contiguous to a respective side of the board. As a result, the first pair of primary straps are snugly fastened to the board with each strap located near a side of the board and extending along the length of the board.

A secondary strap, which comprises a first component and second strap component is fastened at one end to one of the primary straps. The strap, which is approximately one inch wide and approximately two to three feet long, employs a conventional buckle system to permit the effective strap length to be varied.

The procedure for securing and restraining a patient to the trauma board at an accident or other site involves first placing the patient on the trauma board or backboard using an acceptable medical technique such as a three-person log roll.

With the patient disposed on the board, a first strap assembly is employed to secure the patient to the board. A first or upper pair of primary straps, which are located adjacent the patient's shoulder region, are lengthened by releasing the buckle lever on each strap. The primary straps then are loosely drawn over the patient's shoulder and chest region.

The secondary strap, which is attached at one end to one of the primary straps, is looped under the other primary strap with the remaining secondary strap end being suitably connected to a board speed pin. The secondary strap then is adjusted to vary the effective strap length by tensioning the secondary strap whereby the primary straps are drawn together about the patient's upper body region to securely fasten a patient's upper body to the trauma board.

Following the same procedure, a second strap assembly comprising a pair of primary straps and one secondary strap is utilized to secure a patient's lower body portion to the trauma board.

The patient's head is adapted to seat on a headrest which is affixed to a plate releasably bolted to the trauma board.

First and second head component members extend outwardly from the plate. The outboard ends of each member has a female fastener means attached thereto.

A sturdy, light-weight, head hold-down member is placed over the patient's forehead. Webbed strap members extend from each end of the head hold-down member, the free, outboard ends of the strap members having male fastening connectors adapted to snap into the female connectors of the head components. Each strap member includes a buckle system whereby a strap can be suitably adjusted to tension the strap member and reduce its effective length to snugly maintain the patient's head in a fixed position on the headrest. An adjustable chin strap is connected to the head hold-down member and, in use, the chin strap fits over a patient's chin and, thereafter, is tensioned to assist in maintaining the head hold-down member in a relatively fixed position during patient transport. The head hold-down device serves to secure and restrain a patient's head on the trauma board while at the same time permitting a doctor or other medical personnel relatively easy access to a patient's face, ear, eye, nose and neck area without removing the device.

These and other features and advantages of the invention will become more apparent from the following detailed description in which reference is made to the appended drawings.

BRIEF DESCRIPTION OF THE DRAWINGS

FIG. 1 shows a perspective view of a patient positioned on a trauma board and a first strap assembly including a pair of loosely attached upper body primary straps and a secondary strap; and, a second strap assembly including a pair of loosely attached lower body primary straps and a secondary strap;

FIG. 2 shows a perspective view of a patient on a backboard with each strap assembly in FIG. 1 drawn into a snug position and the secondary straps of each assembly are fastened to the trauma board whereby a patient is secured to and restrained on a trauma board;

FIG. 3 shows a fragmentary, perspective view of one end of a secondary strap adapted for movement along at least a portion of the length of a primary strap with the second strap being retained on the primary strap by means of a third webbed strap;

DETAILED DESCRIPTION OF THE DRAWINGS

Figure 4:
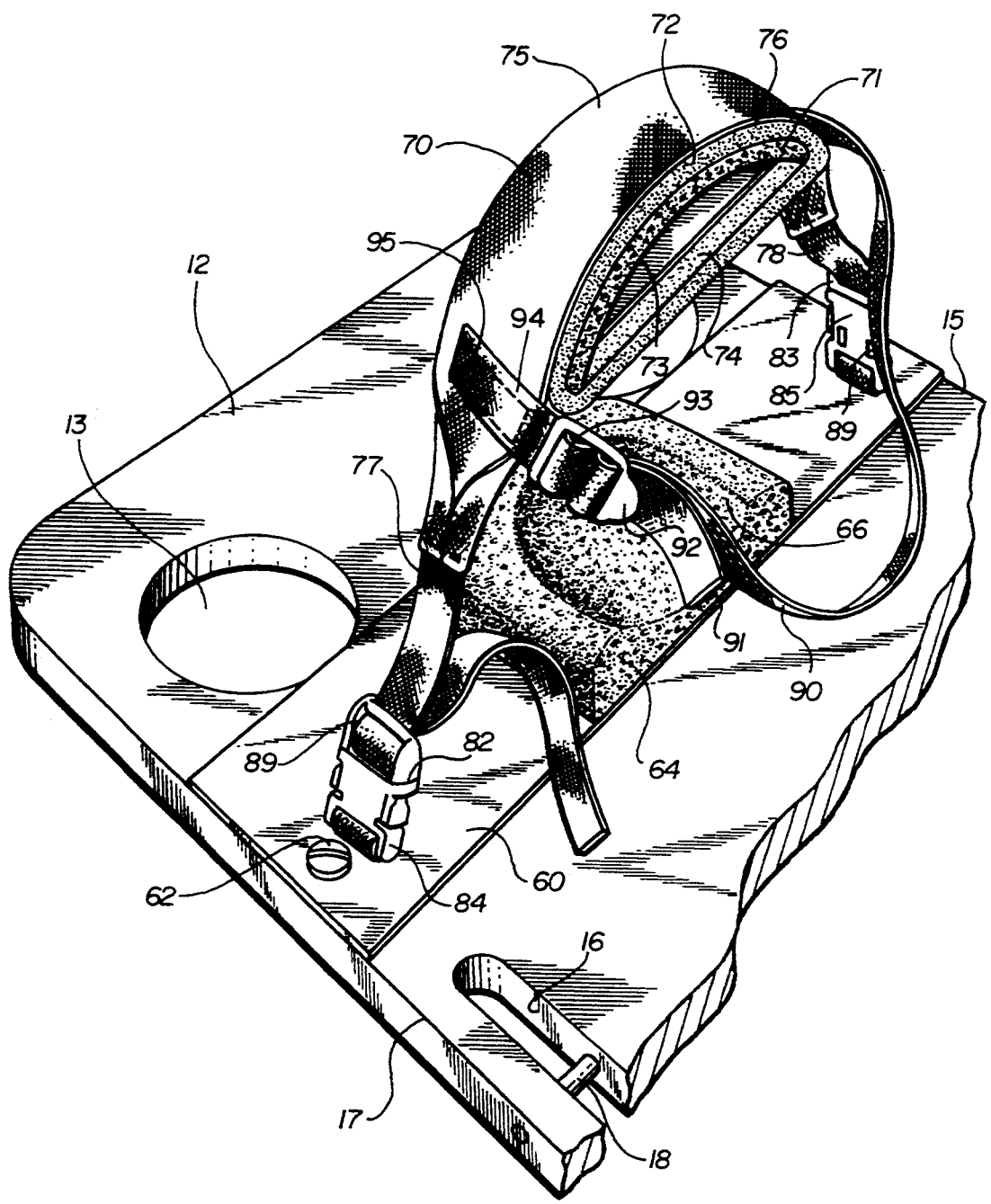
FIG. 4 shows a fragmentary, perspective view of a head hold-down device of the present invention.

Referring to the drawings, FIG. 1 shows a conventional trauma board 12 having a plurality of hand lift openings 13 and a plurality of spaced, elliptical openings 14, 16 which extend along the longitudinal length of board 12 contiguous to board sides 15 and 17.

Conventional speed clip pins 18 extend through a suitable opening 19 whereupon pins 18 are releasably fixed within and traverse openings 14, 16. While it is preferred to utilize clip pins 18, if desired, the present invention could be utilized solely with openings 14, 16 absent pins 18.

FIG. 1 shows two strap assemblies A and B. Assembly A includes primary straps 22, 24 and secondary strap 29. Strap assembly B includes primary straps 26, 28 and secondary strap 30. Each of the straps is a flexible, webbed member made of nylon or other suitable non-porous material.

Primary straps 22, 24, 26 and 28 each have conventional plastic snap clip fasteners 27 located at each end which are adapted to removably fasten to a clip pin 18 in openings 14 and 16. The straps are located in appropriate openings selected to provide the desired patient securement. One end of each of the primary straps is looped as seen at 31, the looped end being attached to a conventional plastic lever buckle 32 slidable along the length of the strap webbing. Movement of buckle 32 serves to vary the effective length of a primary strap. One lever buckle available for use with the primary straps is made by American Card and Webbing, 505 Eighth Avenue, New York, N.Y., Model CB-2. The primary straps are approximately two inches wide with the straps being adjustable to a maximum length of approximately four feet and a minimum effective length of approximately eighteen inches.

Secondary straps 29 and 30 each include a looped end 34 slidable along the length of primary straps 24 and 26, respectively. The distance that secondary straps 29, 30 travel along straps 24, 26 is fixed by a third flexible, webbed strap 38. Strap 38 is sewn at its respective ends to a primary strap and serves to limit the distance strap end 34 travels along the length of straps 24, 29.

In one embodiment, secondary straps 29 and 30 are approximately one inch wide and each strap comprises two strap sections 44, 47. First section 44 comprises a relatively short, flexible, webbed member. A conventional plastic female snap connector 45 extends from the free, outboard end of strap section 44. Second strap section 47 includes two ends, a looped end 34 and an outboard end 46. Plastic, male snap connectors 48 are adapted to slide along the length of strap sections 47 in a conventional manner so as to increase or decrease the effective length of sections 47. Male connectors 48 are adapted to snap into female connectors 45. Upon tensioning or cinching of strap sections 47, by pulling on strap ends 46, the effective length of the secondary straps can be adjusted to bring the primary straps 22, 24 and 26, 28 into somewhat of an hourglass configuration as seen in FIG. 2.

Patches 50, FIG. 3, are made of a suitable non-porous brad-like material and are suitably located on primary straps 24, 26 to which the respective secondary straps 29, 30 are adapted to attach, if desired.

When a primary strap is not in use to restrain a patient, lever buckle 32 can be drawn along the length of the primary strap whereby the primary strap length is varied and the strap rests on the board aligned substantially parallel to board sides 15 or 17.

Preferably, first strap section 44 of each secondary strap 29, 30 is adapted to hang loosely with loop end 53 disposed about speed pin 18. The length of each webbed secondary strap section 44 is approximately 5-7 inches. Second strap section 47 can be adjusted in length from a maximum length of approximately 21-25 inches to a minimum effective length of approximately 4 inches. When not in use, second strap section 47, which is fixed to a primary strap, as described previously, can be drawn up to a suitable, satisfactory effective length and attached to patch 50 whereby the primary and secondary straps are conveniently positioned in an out-of-the-way location until such time as the straps are utilized to secure a patient to trauma board 12.

Figure 5:
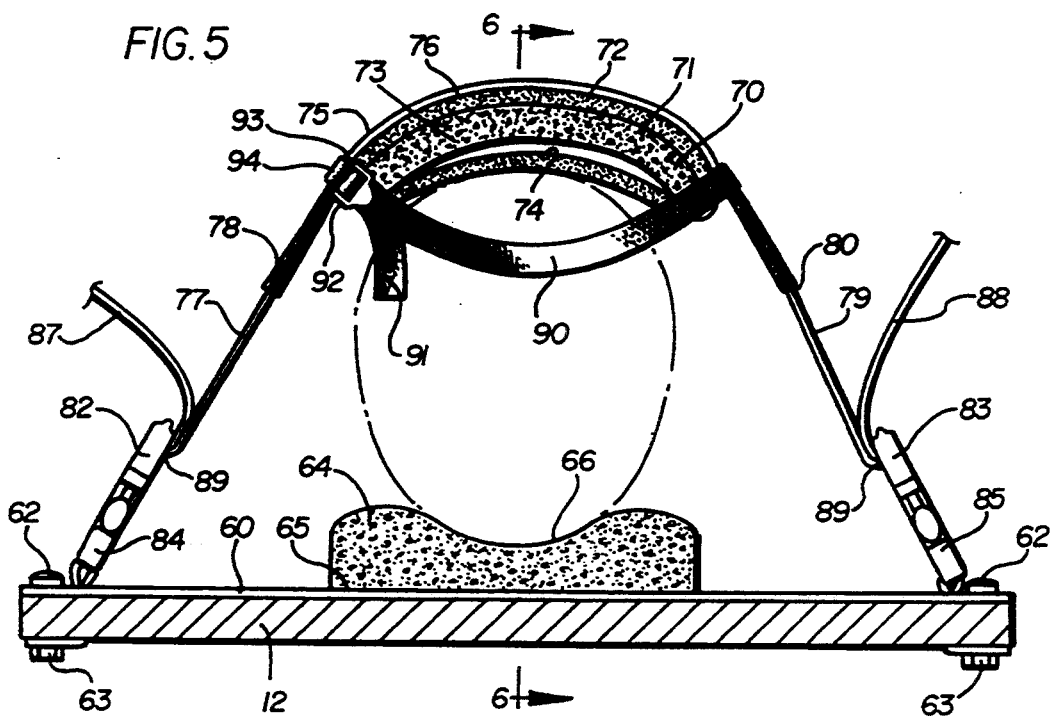
FIG. 5 shows a vertical view of the head hold-down device of FIG. 4.
Figure 6:
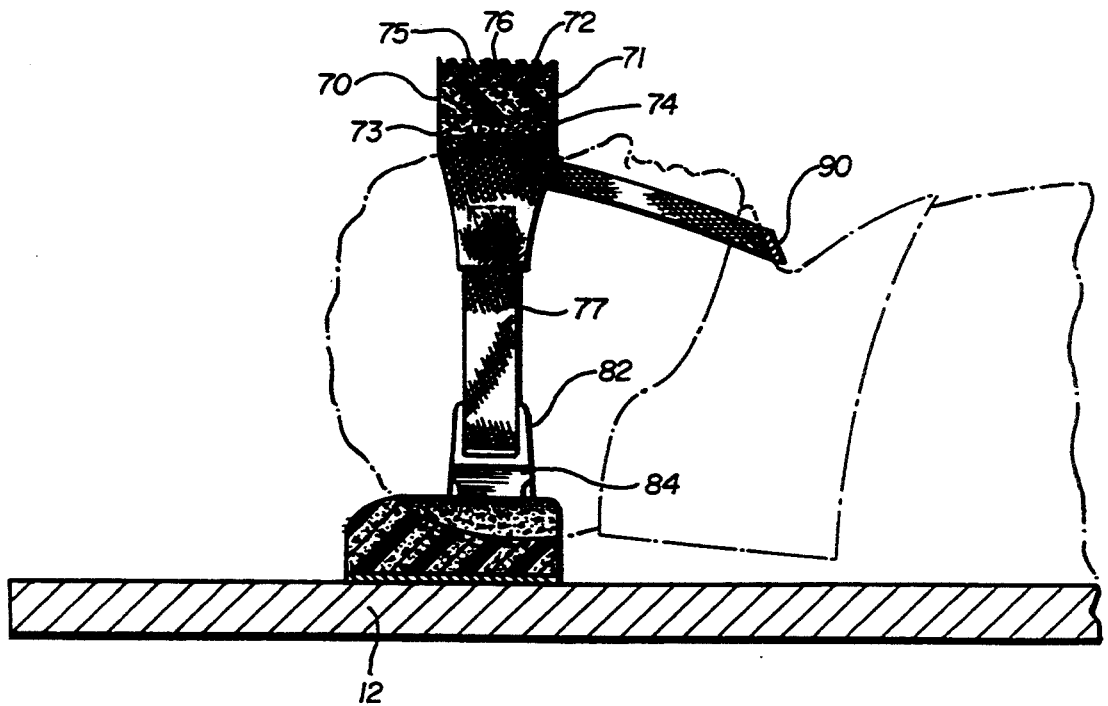
FIG. 6 shows a section view taken along lines 6—6 in FIG. 5.

Turning to FIGS. 4 and 5, plastic strip member 60 is releasably fastened to board 12 by plastic bolts and nuts 62, 63. Headrest 64, made of a suitable, light-weight plastic material such as polystyrofoam, is glued or otherwise adhered to strip 60 along the surface 65 of headrest 64. Preferably, headrest 64 will be covered with a suitable non-porous material which can readily be decontaminated. Headrest 64 has a concave portion 66 in which the occipital region of a patient's head normally is seated when a patient is placed upon board 12.

Head clamp 70, which is adapted to seat on a patient's forehead, comprises curved styrofoam section 71. Section 71 is disposed within an endless elastic sponge-like cushioning sheath 72. Section 71 is preferably covered with a suitable non-porous, synthetic material, for example, a non-porous neoprene rubber material, which can be readily decontaminated of any bodily or other fluids. As seen in FIGS. 4 and 5, the lower section of sheath 72 is spaced from the lower surface 73 of section 71. Upon exertion of suitable pressure on sheath 72, lower surface 73 of section 71 and the top surface 74 of the lower section of sheath 72 are drawn closer together.

A web head wrap 75 extends over the top surface 76 of cushioning sheath 72. Flexible, webbed head strap 77 depends from one end 78 of wrap 75 while webbed head strap 79 depends from the remaining wrap end 80. Head straps 77, 79 are made of a conventional webbed material and are approximately one inch in width and approximately eight inches in length. The outboard ends of each strap 77, 79 have male snap connectors 82, 83 fastened thereto, the fasteners being adjustable by suitable conventional buckle means located along the length of each strap. Male connectors 82, 83 are adapted to snap into plastic female connectors 84, 85 respectively which, in turn, attach to strip member 60. Once fasteners 82, 84 and 83, 85 are snapped together, the effective length of straps 77 and 79 can be adjusted by pulling on the respective strap ends 87, 88 which thread through a conventional adjusting buckle located at 89 to restrain a patient's head on headrest 64.

Webbed chin strap 90 has one end, not shown, sewn onto wrap 75. The remaining chin strap end 91 is adapted to fit into a conventional, adjustable buckle 92 located at the outboard end 93 of webbed buckle section 94 which is sewn at 95 onto wrap 75.

Preferably, all the strap materials are made of a conventional flexible, webbed nylon or other suitable non-porous material which can be cleaned of various bodily or other fluids. All fastener connectors are made of a suitable plastic material which will not interfere with a radiological beam such as an x-ray.

When it is necessary to transport a patient from an accident or other site to a hospital or treatment center, board 12 is moved into position adjacent a patient. The patient then is moved onto the board utilizing an approved technique such as a three-person log roll. Subsequently, the primary straps of each assembly A and B are loosened. It will be noted that the primary straps of assembly A, which overlap the straps of assembly B, are positioned in suitable openings 14, 16 so that the primary straps 26, 28 secure the upper portion of a patient's body whereas primary straps 22, 24 also are located in suitable openings 14, 16 and secure the lower portion of a person's body to board 12.

Straps 26, 28 of assembly B are loosened and slipped over a patient's shoulder and chest area and adjusted so that the loop of the primary strap 28 extends approximately two inches over the patient's longitudinal midline. Secondary strap section 47 then is wrapped about strap 28. First strap section 44 can be attached to a clip pin 18 by looping the section about the pin 18 and fasteners 45, 48 can be connected to one another. Secondary strap 30 is pulled at its end 46 to draw or cinch the secondary strap as seen in FIG. 2 whereby primary straps 26, 28 are drawn together to secure and restrain a patient's upper body to the board.

The same procedure is repeated with respect to the strap assembly A whereby the pair of primary straps 24, 26 are drawn together by secondary strap 29 to secure the lower body portion of a patient to board 12.

While the secondary straps 29, 30 are shown in FIG. 1 as wrapping over and then under primary straps 22, 28, preferably secondary straps 29, 30 are wrapped under and then over the respective primary straps 22, 28, following which the secondary straps are attached to suitable pins 18.

The back of the patient's head is seated in headrest 64. Head clamp 70 is placed over the patient's forehead and male strap connectors 82, 83 are snapped into female connectors 84, 85. The ends of straps 77, 79 then are drawn, as necessary, to tension the straps and fix the patient's head in a relatively immobile position on headrest 64. Chin strap 90 also is tightened to assist in immobilizing the patient's head. The headrest assembly permits a paramedic or other medical personnel relatively easy access to a patient's eyes, ears, nose and mouth, all the while restraining the patient's head from movement.

It is appreciated that, if desired, one skilled in the art could employ other fastener systems for the adjustable lever buckles or snap fasteners disclosed and illustrated herein. What is required is that whatever means are employed, the various primary, secondary and headrest straps must be adjustable in length to permit a strap to vary its effective length and, once a desired length is achieved, the buckle must maintain the strap length. Moreover, it is important that the various materials for the hold-down straps and headrest be materials which will not interfere with permitting a patient to be x-rayed or scanned while immobilized on backboard 12.

While one or more embodiments of the invention have been herein illustrated and described in detail, it will be understood that modifications and variations thereof may be effected without departing from the spirit of the invention and the scope of the appended claims.

What is claimed is:

1. A patient restraint device comprising:
   a trauma board having opposed sides and a plurality of spaced mounting means located along at least said board sides;
   at least one assembly for restraining a patient to said board, said assembly comprising first and second primary straps;
   each primary strap having a first end and a second end;
   each of said first primary strap ends being adapted to be attached to said board mounting means on one side of said board;
   each of said second primary strap ends being adapted to be attached to said board mounting means on said opposite side of said board;
   means for increasing and decreasing the effective length of each primary strap when said primary straps are connected to said board; and,
   a secondary strap adapted to be attached to said board, said secondary strap having two ends and means for increasing and decreasing the effective length of said secondary strap; said secondary strap including means for securing said primary straps together to restrain a patient to said board.

2. A patient restraint device in accordance with claim 1 wherein one of said secondary strap ends is attached to one of said primary straps and movable along at least a portion of the length of said primary strap to which it is attached.

3. A patient restraint device in accordance with claim 2 wherein said secondary strap further includes first and second secondary strap sections;
   said first secondary strap section being adapted to attach to said board and including fastening means for fastening to said second secondary strap section which is connected to said primary strap.

4. A patient restraint device in accordance with claim 2 and further including a third strap means having two ends, said third strap means being attached to said one primary strap and including means for limiting said secondary strap to travel along a portion of said primary strap.

5. A patient restraint device in accordance with claim 1 wherein said assembly is adapted to restrain a first portion of a patient's body to said board; and further including a second assembly, said second strap assembly comprising:
   a pair of said first and second primary straps, each of said straps having two ends and adapted to be attached to said board with one primary strap being attached at its ends to one side of said board and said second primary strap being attached at its ends to said remaining side of said board; and
   a secondary strap adapted to be attached to said board and having two ends; and,
   means for increasing and decreasing the effective length of said secondary strap whereby said secondary strap is adapted to draw said primary straps together to restrain a second portion of a patient's body to said board.

6. A patient restraint device in accordance with claim 5 wherein one of said secondary strap ends is attached to one of said primary straps.

7. A patient restraint device comprising:
   a trauma board having opposed sides and a plurality of spaced mounting means located along at least the spaced sides of said board;
   at least one assembly for restraining a patient to said board, said assembly comprising first and second primary straps;
   each primary strap having a first end and a second end;
   first primary strap ends being attached to said board mounting means on one side of said board;
   said second primary strap ends being attached to said board mounting means on said opposite side of said board;
   means for increasing and decreasing the effective length of each primary strap;
   a secondary strap having two ends;
   one secondary strap end connected to one of said primary straps and movable along at least a portion of the length of said primary strap to which it is attached;
   said remaining end of said secondary strap being adapted to attach to said board mounting means; and,
   means for increasing and decreasing the effective length of said secondary strap whereby said secondary strap is adapted to draw said primary straps together to restrain a patient to said board.

8. A patient restraint in accordance with claim 7 and further including a second of said assemblies which comprises a pair of said primary straps, each primary strap having two ends which are attached to one board side; and,
   said secondary strap including means for increasing and decreasing the effective length of said secondary strap to draw said primary straps together to secure a patient to said board.

9. A patient restraint device comprising:
   a trauma board having a plurality of spaced mounting means located along at least the spaced sides of said board;

at least one strap assembly, said assembly comprising first and second primary straps each having two ends;

each of said first primary strap ends being attached to said board mounting means on one side of said board;

each of said second primary strap ends being attached to said board mounting means on said opposite side of said board;

means for increasing or decreasing the effective length of each of said primary straps;

a secondary strap having two ends with one of said ends being connected to one of said primary straps for movement along at least a portion of the length of said primary strap;

said remaining end of said secondary strap including means for connecting said secondary strap to said board; and, said secondary strap including means for increasing or decreasing the effective length of said secondary strap.

10. A restraint device in accordance with claim 9 wherein said secondary strap comprise a first section and a second section;

said first secondary strap section being connected to said primary strap for movement along at least a portion of said primary strap;

said second secondary strap section being connected to said board; and, means for releasably fastening said first and second secondary straps together.

11. A restraint device in accordance with claim 9 or 10 and further including a second assembly comprising a pair of said primary straps and one of said secondary straps whereby said first assembly is adapted to restrain one portion of a patient's body to said board and said second assembly is adapted to restrain a second portion of a patient's body to said board.

12. The device of claims 1, 7 or 9 wherein said straps are fabricated from a web-like, non-porous material.

13. The device of claims 1, 7 or 9 and further including a patient head restraint, said head restraint comprising a headrest;

a restraining member having two ends adapted to seat solely on a patient's forehead;

a head restraining strap depending from each restraining member end;

means for connecting said head restraining straps to said board; and, means for adjusting the effective length of said head restraining straps;

said head restraining device permitting access to a patient's face, mouth, nose and ears while a patient's head is restrained to said board.

14. The device of claim 13 and further including a strap member removably fastened to said board;

fastening means on said member for releasably connecting to said head restraining straps; and, said headrest being fixed to said strap member.

15. The method of restraining a patient on a trauma board having opposed sides and a plurality of board mounting means and at least one strap assembly which comprises a pair of primary straps and a secondary strap, each strap having two ends and means for adjusting the effective strap length, said method comprising:

(a) mounting one of said primary straps so that each end of said primary strap is connected to said board mounting means on one side of said board and said second primary strap having each end connected to said board mounting means on said opposite board side;

(b) connecting one end of said secondary strap to one of said primary straps;

(c) orienting said first primary strap of said assembly toward the longitudinal midline of a patient located on said board;

(d) orienting said second primary strap of said assembly toward the longitudinal midline of said patient;

(e) wrapping said secondary strap about said oriented primary strap to which it is not connected;

(f) connecting said remaining secondary strap end to said board means; and, (g) adjusting the effective length of said secondary strap to cause said primary straps to draw together to restrain at least a portion of said patient onto said board.

16. The method of claim 15 and further utilizing a second of said strap assemblies and carrying out steps (a)-(g) with said second strap assembly whereby said first assembly secures one portion of a patient's body to said board and said second assembly secures a second portion of a patient's body to said board.

* * * * *